United States Patent [19]

Canino

[11] Patent Number: 4,672,196
[45] Date of Patent: Jun. 9, 1987

[54] METHOD AND APPARATUS FOR MEASURING PROPERTIES OF THIN MATERIALS USING POLARIZED LIGHT

[76] Inventor: Lawrence S. Canino, 4815 Milne Dr., Torrance, Calif. 90505

[21] Appl. No.: 576,330

[22] Filed: Feb. 2, 1984

[51] Int. Cl.[4] ............................................. G02F 1/01
[52] U.S. Cl. .................................. 250/225; 250/560; 356/369
[58] Field of Search ............................. 356/364–370; 250/225, 560, 561

[56] References Cited

U.S. PATENT DOCUMENTS

| | | | |
|---|---|---|---|
| 3,697,180 | 10/1972 | Mori et al. | 356/367 |
| 3,880,524 | 4/1975 | Dill et al. | 250/225 |
| 4,077,720 | 3/1978 | Kasai | 356/369 |
| 4,210,401 | 7/1980 | Batten | 356/369 |

*Primary Examiner*—David C. Nelms
*Attorney, Agent, or Firm*—Don A. Hollingsworth

[57] ABSTRACT

A method and means for measuring and/or determining characteristics of a material by analyzing the characteristics of an energy beam incident upon and affected by the sample. Polarized radiant energy reflected and/or transmitted by the material sample is analyzed to infer optical properties such as index of refraction, and physical properties such as material thickness. The invention is not subject to the disadvantages of prior art measuring systems, in that absolute detected light values are not used, measurement of varying wavelengths of light are not necessary, surface defects contribute a balanced effect in the calculations so as to effectively cancel out, highly accurate angular measuring devices are not needed, precision nulling instruments are avoided, system parameter drift effects upon the measurement is avoided, inter alia. According to the invention, a method and means are provided for measuring an optical property of a thin material sample having a transmission efficiency of greater than zero for an impinging beam of radiant energy. A source beam of radiant energy at a given wavelength and of varying polarization direction is provided, and the polarization-varying beam is directed onto an entry surface of the thin material sample at a predetermined angle with respect thereto. The beam leaving the sample is analyzed to determine the relative amplitudes of first and second polarized components thereof. The optical property of the sample is determined from a mathematical model equating the optical property to a relationship between said wavelength of the source beam, the predetermined angle, and the results of detecting and analyzing the beam exiting the sample.

20 Claims, 12 Drawing Figures

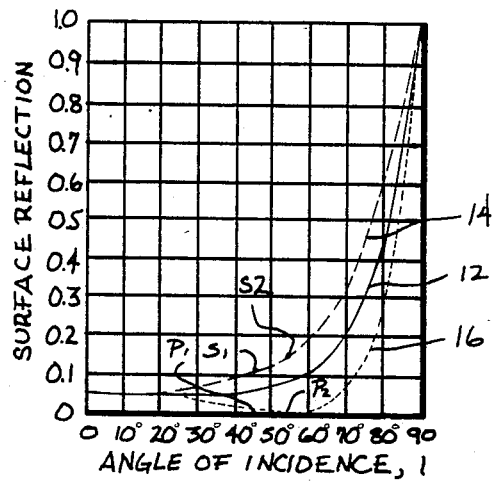
Fig 1
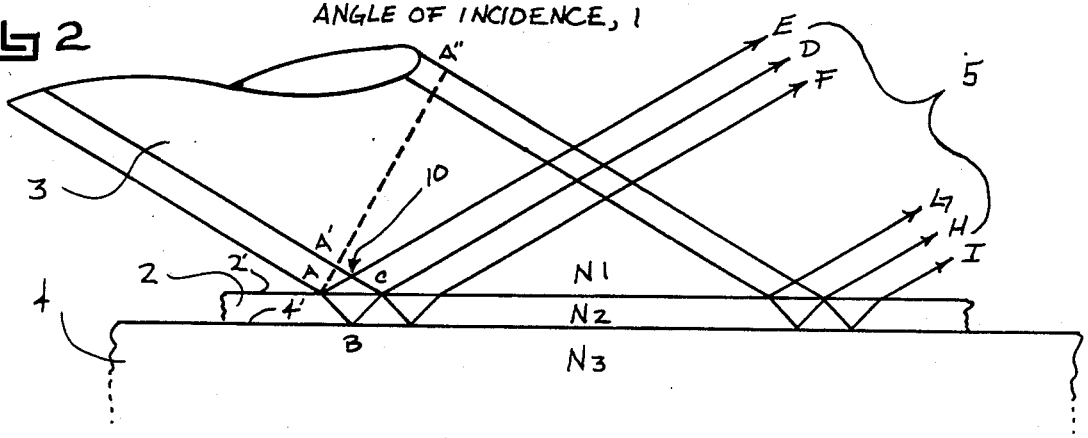
Fig 2
Fig 3 (PRIOR ART)
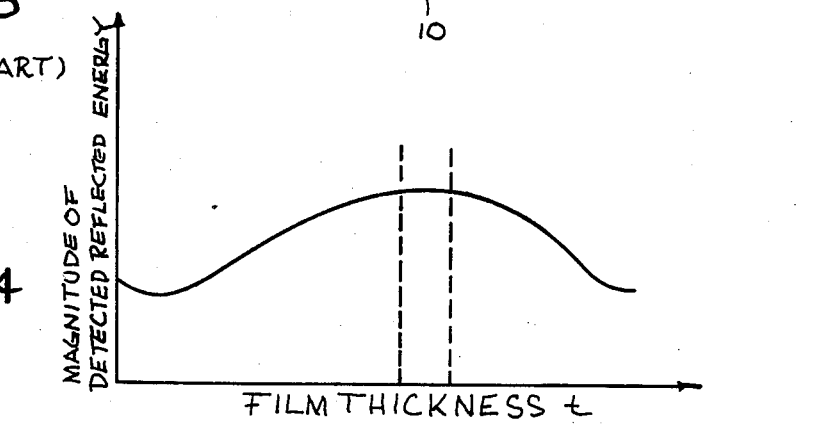
Fig 4

METHOD AND APPARATUS FOR MEASURING PROPERTIES OF THIN MATERIALS USING POLARIZED LIGHT

BACKGROUND OF THE INVENTION

1. Field of the Invention

This invention is related to the field of measuring material sample characteristics by the interaction of energy with matter. More specifically, the invention concerns measuring and/or determining characteristics of a material by analyzing the characteristics of an energy beam incident upon and affected by the sample. In the described embodiments, polarized radiant energy reflected and/or transmitted by the material sample is analyzed to infer optical properties such as index of refraction, and physical properties such as material thickness.

In this description, the term "thin film" will be used to define any material whose thickness is to be measured. For ease in describing the invention, however, hereinafter the term will refer to a material that can be deposited as a thin film by a variety of processes such as chemical, mechanical, or high-vacuum evaporation techniques. Typically, such thicknesses are in the vicinity of near zero to 20,000 angstroms. Since film thickness test results using radiant energy beams must depend, at least in part, upon the energy beam traversing through the body of the material under test, the material to be tested must be either transparent transluscent or at least partially transmissive to the impinging energy beam.

2. Brief Description of the Prior Art

In addition to the obvious mechanical devices used for measuring the thickness of materials (considered rather thick in comparison to the types of materials to be measured using the devices and methods of the present invention), a variety of known techniques and devices have been conceived for measuring the thickness of a thin film material using radiant energy beams, and in particular, laser beams.

One such method employs the use of an ellipsometer, that is, a spectrometer equipped with polarizing prisms and retardation plates, used primarily in the analysis of elliptically polarized light in the study of thin evaporated films. In ellipsometry, a beam of collimated light is directed through a polarizer and subsequently through a quarter-wave retardation plate, after which it is reflected by the thin film under test. This reflected beam is then directed through a second polarizer which is generally called an analyzer. Two of the three optical elements are then interactively rotated so as to produce extinction of the beam exiting the second polarizer. The angular positions of the elements are then accurately measured and used to solve for thin film thickness.

As will be discussed in detail later, incident light impinging upon the surface of a thin film sample at a given angle will be reflected in different amplitudes, depending upon the angle of polarization. Accordingly, by knowing the incident angle, the index of refraction of the material, and the amplitudes of the two coherent plane-polarized elements of the incident beam, sufficient information from a detector detecting the amount of reflected light attributed to each of the two beam elements can be derived to determine the thickness of the film. While ellipsometry has been satisfactory for many applications in determining thickness of thin film materials, this method of measurement uses mechanical rotation of optical elements to find a power null and requires precision angular measurement of the angles of rotation. While these are not great disadvantages in slow manual operation where the operator rotates the elements by hand while seeking a null and then takes readings from angle verniers, they are expensive to automate. To automate such an ellipsometer would require servos to rotate the elements interactively to find a null, as well as precision angular encoders to determine the precise angles needed for accurate measurement.

A second method of determining thicknesses for thin films is by using a variable frequency or variable wavelength light source, again directing the light beam from the source at a given precise angle relative to the surface of the sample under test. By knowing the index of refraction for the material and noting the angle of incidence of the beam, and by determining the precise wavelength of the incident light at which a maximum amount of reflected light is detected, the thickness of the sample can be determined. Incremental errors having a magnitude of some multiple of $\frac{1}{2}$ wavelength of the incident light must be accounted for in the final results. This is due to the fact that the light traversing the thickness of the film and combining with the reflected light from the upper surface thereof reinforces the latter to a maximum degree when the distance traveled through the film is equal to a full wavelength of the incident light, and cancels the reflected light to a maximum degree when the distance travelled is one-half wavelength. Variations between minimum (maximum cancellation) and maximum are cyclically repeated as a function of change of distance travelled through the sample so that an intensity measurement of a particular magnitude of reflected light will occur twice each cycle, and, of course, there may be more than one cycle of phase difference between the beam portions reflected from the top and bottom surfaces of the sample. This $\frac{1}{2}$ wavelength increment error is inherent in all thin film measuring schemes using reflected light beams. The problem is greatly magnified in the variable frequency technique, however, since the wavelength is varying and thus adds another variable to the already complex formula for calculating thickness, and some additional information must be fed into the computation before reliable results can be obtained. Again, although effective for measuring small thicknesses of thin film material, a number of disadvantages of this technique can be readily appreciated. First, when a peak is found in the reflected beam, the exact wavelength of the varying frequency light source must be determined with expensive and precision instrumentation. Moreover, a plotted curve for the relationship of reflected intensity versus wavelength will show that the knee of the curve is rather broad, having a peak with a slowly changing amplitude making the selection of the actual peak point on the curve indeterminate. As a result, an inherent tolerance figure must be accounted for when the determination is made that a peak in reflected intensity level has been detected. Another critical factor in establishing the credibility of a thickness measurement with this technique is the fact that the index of refraction for the particular material being measured must also be known at the exact frequency of the incident light which produced the peak in reflected energy. This determination is nesessitated by the dispersion parameter of the material under test, i.e., the change of index of refraction with change of wavelength of incident light. While a number of machines have been developed to measure the dispersion of the film the need for inputting the dispersion factor into the formulas for calculating the film thickness adds significantly to the cost of the procedure and renders the procedure impractical for nominal users. Moreover, the exact dispersion factor for a given material changes with deposition process variations. Accordingly, where dispersion factors enter into measurement analyses, only approximate or assumed values can be used.

A third, and more simplified, method for measuring film thickness involves the impinging of a single wavelength light beam onto a surface of a sample and measuring both the intensity of the incident beam and that of the reflected beam. Again, with the known angle of incidence, the known index of refraction of the material, and the precise wavelength of the incident beam, the ratio of intensity of reflected beam to that of incident beam gives the amount of loss due, for a clean sample, to the interference effects of the beam elements reflected from the upper and lower surfaces of the sample. Thus, by knowing the amount of cancellation or reinforcement, the path length of the incident beam through the material in terms of incident beam wavelength can be determined, and through mathematical calculation, the thickness of the film can be determined. One of the major disadvantages of this type of simplified system is the fact that the intensity level of the reflected beam is not necessarily due in total to the light wave interference effects. Any defects in the material at the point of impingement of the beam, such as scratches, dust particles, surface irregularities, and the like, will account for some percentage of the loss of light from source to detector. Accordingly, several regions on the sample must be measured, and until consistency of results are determined, the true thickness of the film cannot be ascertained. Since some surface defects can occupy relatively large regions for such samples as integrated circuits, or even span the entire surface (as in a mottled surface), there may not be sufficient surface area available to permit the number of measurements needed for eliminating the contribution of defects from the final results.

In the aforementioned prior art system, one must either (1) produce and measure very precise mechanical rotations, or (2) measure the absolute quantities of light striking photodetectors with an essentially defect-free optical path and thin film sample, or (3) determine the peak value of a slowly varying light level and know the precise wavelength at that peak and also assume an index at that wavelength because of dispersion.

Accurate film thickness test results thus depend upon absolute measurements of the amount of light detected, and drift of system parameters, for example temperature, power supply voltages, surface blemishes, detector electrical and mechanical position drift, noise, and the like, all contribute to thickness calculation errors, because the detector output has no information in it to discern the difference between loss of light energy due to the wave interference effects and that due to misadjusted, defect-altered, or drifting parameters.

SUMMARY OF THE INVENTION

It is an object of the present invention to provide a method and device for measuring the thickness of thin film materials not subject to the above-mentioned disadvantages. More particularly, the invention virtually eliminates the need for entering into the thickness measurement calculations, inputs concerning drift parameters, intrinsic noise components, source power variation, optical path losses, sample scratch or blemish defects, sample diffusion aberration, positional variation of detector response, detector temperature variation, and electronic circuit drift, among others. These advantages are largely attributed to the use of more than one polarization characteristic of the source beam and the use of more than one incident angle of the beam. With more than one polarization characteristic of the source beam, only relative, rather than absolute, measurements of the reflected light are required.

Additionally, differing polarizations of the reflected beam may be made to time share the same location of a single detector. The use of a relatively high frequency of time sharing measurement relative to the time change associated with system drift parameters virtually eliminates the effects of system drift. Moreover, the use of common optical paths and devices, and of common electronic circuitry with which the energy source beam and detector circuitry, respectively, are interleaved in time, all tend to null out any otherwise deleterious effects which would have to be accounted for if separate optical paths and separate electronic detector circuitry were required.

Basically, the present invention involves a method and apparatus for measuring the thickness of a thin material sample having a transmission efficiency of greater than zero for an impinging source beam of radiant energy. The index of refraction of the sample being measured must be known at the given wavelength of the source beam. Alternately, if the thickenss is known, the index of refraction can be determined in an analagous manner. Further, in an alternate preferred embodiment of the invention, both an unknown thickness and an unknown index may be determined. Since only a single wavelength of light is used, dispersion factors do not enter into the thickness measurement calculations.

Whether time shared or not, a pair of such radiant source beams are directed onto an entry surface of the material sample, each beam having two components of different angles of polarization, the two beams also having different angles of incidence to the entry surface. The two beams reflected (or those transmitted) by the sample are detected and analyzed to determine the ratio of detected energy for the two components of each beam. The thickness of the sample is then determined from a mathematical model equating material thickness to a relationship between the given wavelength of the source beams, the given index of refraction for the material under test, the angular values of the two incident source beams, and the amplitude ratio comparisons of the two components of each of the two beams.

In this description, the beam or beams reflected from a sample are analyzed for determination of sample thickness and/or index of refraction. Obviously, if desired or more convenient for a given sample, the beam or beams transmitted through the sample could be analyzed without departing from the scope or spirit of the invention. Thus, it is to be understood that where this description uses the term "reflected", the term "transmitted" could be substituted, assuming that the different beam paths were accounted for in the mathematical calculations.

In one preferred embodiment of the invention, a single wavelength source beam from a single laser unit is split into a plurality of beams eventually to converge at a single point on the sample. The polarization direction of each beam is varied, either incrementally or continuously, to produce a time-shared relationship, with a first polarized component of the beam polarized in a first direction, and a second polarized component of the beam polarized in a second direction angularly displaced from the first direction, and preferably by 90 degrees.

The polarization-varying beam is directed onto the entry surface of the thin film material sample at a first predetermined angle with respect thereto, and the beam reflected by the sample at the first predetermined angle is detected and analyzed to determine the ratio of relative amplitudes of reflected first and second polarized components. When the polarization-varying beam is directed onto the entry surface of the thin material sample at the second predetermined angle with respect thereto, the beam reflected by the sample at the second predetermined angle is detected to determine the ratio of the respective amplitudes of reflected first and second polarization components. A comparison is then made of the ratio of first-to-second component amplitudes at the first predetermined angle with the ratio of first-to-second component amplitudes at the second predetermined angle. The thickness of the sample material is then calculated from a mathematical model equating material thickness to the relationship discussed above.

Although, theoretically, any angle between the two angularly displaced components of each beam can produce the desired results in accordance with the concepts of this invention, it is preferred, and substantially reduces measurement time that the first and second polarized components be at right angles to each other, defining S and P beam components for the beam relative to the sample. As used herein, the S polarization angle of the beam is that polarization angle which is parallel to the plane of the sample, and the P polarization angle is oriented perpendicular to the planar surface of the sample.

As suggested above, by varying the polarization direction of the source beams to produce the first and second polarized components is meant that the single beam, of single wavelength, is time shared insofar as beam polarization angle is concerned. In a straightforward manner of effecting such time sharing, a pair of polarization plates may be alternately placed in the path of the beam emanating from the laser so as to effectively transmit serial packets of alternately changing polarization direction.

Alternatively, the beam exiting the laser may be passed through a quarter wave plate to convert a linearly polarized source beam (assuming the laser device is of the type to produce it) to a circularly polarized light beam. The latter beam is then directed through the hollow shaft of a rotating electric motor which houses and rotates a polarization plate at a prescribed angular velocity. The overall effect of this combination of elements produces a light beam of continually varying polarization direction. Although either the incrementally-changing or continuously-changing polarization varying technique may be used in accordance with the broadest aspects of the invention, certain advantages are attributed to each alternative. Basically, however, the major difference lies in the more simplistic detection techniques and analyzing computations using the alternately changing procedure.

In a preferred embodiment of the invention, a unique beam splitting device is employed. Since it is advantageous to produce a plurality of parallel light beams of equal energy level and of predictable polarization direction, prior art techniques for beam splitting cannot be used. As an example, a diffraction grating, while issuing well defined geometrically acceptable multiple light beams, tends to distort the polarization character of the incident beam and produces "ghosts" of unwanted light energy at unwanted positional locations. Additionally, diffraction gratings produce nonparallel unequal energy levels of the issuing beams. Like difficulties are associated with the use of beam splitting cubes which are particularly prone to serious errors due to mechanical misalignment. The preferred beam splitter according to the present invention develops nearly equal energy parallel beams not subject to mechanical misalignment.

The most sensitive element to drift, in a measurement apparatus using laser beams to measure film thickness, is the detector. Further, a major contribution to the errors encountered in measuring film thickness involves the requirement for accurately measuring absolute light values. This can render data useless when the source beam is unknowingly directed onto a part of the sample containing a scratch, dust particle, or surface blemish. By interleaving in time (intermittently or continuously) S and P polarized source beams, both S and P polarized beams hit the same spot on the specimen and would be equally affected by the surface defect. Similarly, by using the same detector for detecting a single beam containing the S and P components, any differences in measurement values due to circuit drift or detector noise, as well as any defects in the optical path leading to the detector, are eliminated.

By observing the amount of reflected (or transmitted) energy from the specimen for the S and P polarization angles, wherein the S and P polarizations are alternately or continuously varying and sampled at a relatively high rate, it would be a simple matter for a computer to compare the relative magnitudes of S and P and use the result to infer the thickness of the film. By taking the ratio of S to P levels, any surface defects of the aforementioned type would have the effect of lowering the magnitude of P by a fixed percentage and simultaneously lowering the magnitude of S by the same fixed percentage. Accordingly, when the ratio between the two are taken, the losses due to the defects or drift parameters are virtually eliminated.

The invention is not limited to the use of only two angles of incidence of impinging source beams. On the contrary, advantages not obvious from known schemes, wherein only a single angle of incidence is used, can be realized using more than two beams of differing incident angles (each having varying S and P components, however).

The more angles of incidence, the more information that can be gathered. For example, if two angles of incidence are used and the index of refraction is known, the thickness of the sample can be determined, as discussed supra. If the thickness is known to within a limited range (very often the case in controlled film depositing processes), one angle of incidence can be used to infer the index or thickness, and two angles of incidence allow measurement of thickness and index of refraction, both being previously unknown. With four angles of incidence, the thickness and index of refraction may be calculated over many cycles, i.e., by using many ratios of S to P created by the destructive and constructive interference effects of the reflected and refracted light in the sample. Using multiple angles of incidence has additional benefits. In an embodiment of the invention using continuously varying polarization of the incident beam, the solution for finding index or thickness is similar to finding the crossing point of two curves in a graphical plot.

BRIEF DESCRIPTION OF THE DRAWINGS

The invention will now be described in greater detail having reference to the accompanying drawings, in which:

FIG. 1 is a graphical representation of the magnitude of surface reflection versus angle of incidence for unpolarized light, light polarized in the plane of incidence, and light polarized perpendicular to the plane of incidence;

FIG. 2 shows a representation of the paths taken by an incident beam of radiant energy as it is reflected by and transmitted through a thin film sample;

FIG. 3 is an illustration of a prior art method of measuring thin film thicknesses using a radiant energy beam;

FIG. 4 is a graphical representation of magnitude of reflected energy versus film thickness for a specific polarization angle of incident energy;

DETAILED DESCRIPTION OF THE PREFERRED EMBODIMENTS

Figure 5:
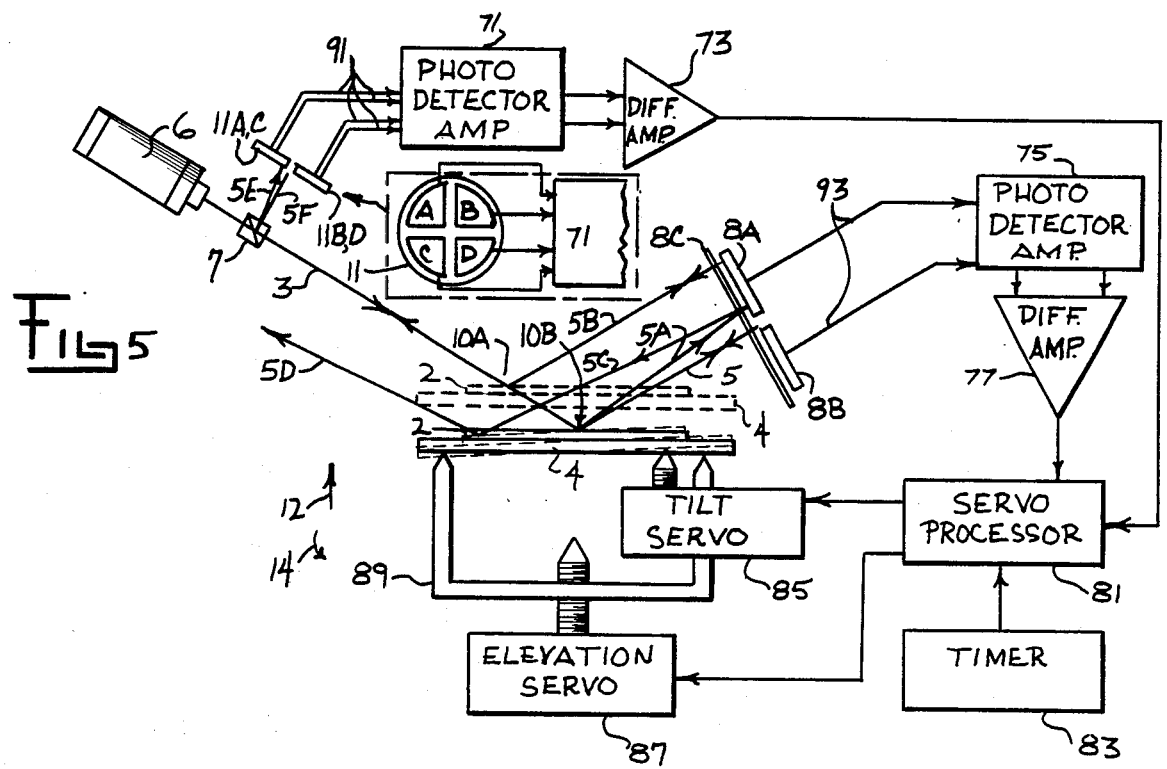
FIG. 5 shows a system, in accordance with the invention, for sensing and for automatically correcting errors in tilt and elevation of the sample under test relative to the source energy beam apparatus and detector apparatus.

FIG. 1 is a graphical representation of the magnitude of surface reflection versus angle of incidence of an impinging light beam. The particular values of the axes of the graph are examplary only and are specific to the reflection from a single air-glass interface for a glass with an index of about 1.5. The solid line 12 represents the surface reflection characteristics of unpolarized light, the dashed line 14 represents the reflection of light polarized in the plane of incidence, and the dotted line 16 represents the reflection of light polarized perpendicular to the plane of incidence. It can thus be seen that there is a variation of the reflection from an air-glass interface as a function of angle of incidence of an impinging energy beam. Further, it is to be noted that the dotted line 16 drops to substantially zero reflectivity at about a 55 degrees angle of incidence. This angle is referred to as Brewster's angle which occurs when the reflected and refracted rays are at 90 degrees to each other. Thus, at the polarization angle depicted by line 14, about 15 percent of the light is reflected at Brewster's angle, while the polarization angle producing line 16 indicates that the incident energy beam is completely transmitted. The significance of the basic principle illustrated in FIG. 1 will become evident in the discussion of subsequent figures.

When the surface-to-surface separation is small of the sample whose thickness is to be measured, i.e., when such separation is on the order of the wavelength of the impinging light beam, then interference between the light reflected from the surfaces involved will occur and the net reflectivity of the surfaces will differ markedly from that merely of a single air-glass interface. FIG. 2 is offered to illustrate this phenomenon.

In FIG. 2, the incident beam 3 of parallel light is shown to have a wavefront A—A" intercepted by a pair of reflecting surfaces 2' and 4'. At some instant, the wavefront A—A" strikes the first surface 2' at A. The point on the wavefront at A travels through the space between the two surfaces 2' and 4' and strikes the second surface 4' at B where it is partially reflected. The reflected wave from point B then travels upward to pass through the first surface again at C. Meanwhile, the point on the wavefront at A' has been reflected at point C, and the two paths recombine at this point. If the incident wave and reflected wave from point B arrive at C in phase, they will reinforce each other or add together, due to constructive interference, to represent an amount of light energy radiating toward D which is greater than that which is merely reflected by the surface 2' at C. On the other hand, if the incident and reflected waves reaching point C arrive one-half wavelength out of phase, they will cancel, due to the destructive interference between the two wavefronts. Only simple ray elements are shown in FIG. 2 to illustrate the effect of the combining of incident and reflected waves propagating toward point D, and if other ray elements of incident beam 3 along wavefront A—A" were shown in FIG. 2, the same constructive and destructive interference phenomenon will be evident in the ray elements directed towards all points between D and H.

Thus, the reflected beam 5 represents some portion of the incident beam 3, and its magnitude is determined, not only by the surface reflection of surface 2' and discussed in connection with FIG. 1, but also by the refracted and reflected beam traveling along the path ABC and other similar paths across the width of the beam 3. In this connection, it must be appreciated that the beam width is typically 30 to 100 or more times the thickness of the sample, the dimensions of FIG. 2 being scaled for ease of understanding and clarity.

Obviously, if the distance ABC through the material of sample 2 is not precisely equal to an even or odd number of half wavelengths of the incident beam, values of reflected light in beam 5 will vary between the constructively reinforcing maximum and the destructively interfering minimum. In the determination of the phase relationship at C, the index of refraction of the material 2 must be taken into account as well as the phase change which occurs upon reflection of the incident beam at surface 2'. The phase change at surface 2' is an important consideration in the implementation of the present invention and will thus be investigated in more detail, having reference to "Modern Optical Engineering" by Warren J. Smith, McGraw-Hill Book Company, Copyright 1966, Pages 13 and 14.

The phase change at surface 2' occurs when light (beam 3) traveling through a low index medium $N_1$ is reflected from the surface of a high index medium $N_2$. The phase then abruptly changes by 180 degrees or one-half wavelength. No phase change occurs when the indices are encountered in reverse order, for example as between sample 2 having a high index of refraction $N_2$ and substrate 4 having, for example, a low index of refraction $N_3$. Thus, with the relative indices as indicated in FIG. 2, there is a phase change at C for the light following the path A'CD, but no phase change at B for the light reflected from the lower surface 4'.

The difference between the optical paths ABC and A'C determines the phase relationship of the beam 5 directed toward point D. Since the index of refraction is inversely related to the velocity of light in a medium, and considering the phase change which occurs on reflection at surface 2', it is a simple matter of applying basic optical analysis to show that the number of cycles for the path A'C is given by the equation $\frac{1}{2} + N_1 A'C/\lambda$. The one-half cycle term in the equation represents the reflection phase change at B of surface 2'. Similarly, the number of cycles for the path ABC is given by the formula $N_2 ABC/\lambda$. Using these formulas, if the values of the two formulas differ by an integer, the waves will reinforce; if they differ by an integer plus one-half, they will cancel. It is clear that if one considers the difference between the two path lengths (arrived at by multiplying the above number of cycles by the wavelength $\lambda$) exactly equivalent results are obtained when the difference is an integral number of wavelengths (for reinforcement) or an integral number plus one-half wavelength (for cancellation). Thus, for FIG. 2, the optical path difference (OPD) is given by the formula
ti $OPD = \lambda/2 + N1A'C - N2ABC$, noting that the phase change is taken into account by the term $\lambda/2$ in the formula.

Consider now the prior art arrangement of FIG. 3 incorporating the principles discussed in connection with FIGS. 1 and 2. In FIG. 3, a laser light source 6 generates an incident beam 3 impinging a sample 2 supported by substrate 4. A reflected beam 5 is intercepted by a detector 8 which outputs an electrical representation 9 of the amount of energy in reflected beam 5. The angle of incident I and angle of reflection R are measured from a vertical line extending from the point of impingement 10 normal to the surface of sample 2. A beam splitting cube 7 is inserted in the path of incident beam 3 to sample the energy level of beam 3 by a photodetector 11 having an electrical output 13 to be compared with the electrical output 9. By incorporating the principles of reflection from surface 2' according to FIG. 1 and accounting for the phase change at surface 2' and the contribution of reflected energy from surface 4', an expected amount of light energy in reflected beam 5 can be predicted. By measuring the energy levels of the incident and reflected beams, and knowing the index of refraction of the materials contributing to the reflection of the beam 5, the thickness of sample 2 can be calculated.

There are several significant disadvantages to the prior art method shown in FIG. 3 which result in inaccurate and perhaps useless information as to the true thickness of sample 2. First, in the case where the incident beam 3 impinges a defective area of sample 2, the loss of reflected and refracted energy contributing to the net energy value for reflected beam 5 cannot be anticipated or taken into account in the final results, since the amount of such contribution to the reflected beam 5 is totally unknown and not ascertainable. To avoid errors using this method, the laser beam or sample is moved so as to impinge the surface at a new point of impingement 10, and the calculations are repeated to determine consistency with the first reading. Even if the two readings are the same, it is often the case that a defect spanning the two selected points of impingement would similarly affect the reflected beam or that a continuous surface imperfection would cause similar diffusion of the light, so that a third measurement or more must be made.

Secondly, since a reasonable time must be alloted for repositioning the laser beam or sample, in the meantime the detectors 11 and 8 may have changed their characteristics due to temperature change, voltage variations, and the like. Moreover, since two separate detectors are used, one for the incident beam 3, and one for the reflected beam 5, a defect (e.g., a speck of dust) on one of the photodetectors would contribute an offset error in the ultimately calculated results. While the latter-mentioned problem might be avoided by measuring a sample of known thickness and adjusting the system for an accurately calculated result, there is no way of determining whether or not a subsequent measure of an unknown sample would be made under a changed environment where another speck of dust or fiber would have, in the meantime, been encountered. In any event, the sensitivity variation of the detector over time and its environment cannot be practically controlled. Thus, wide tolerances exist, and the net result may not be acceptable, being merely an educated guess at the material thickness.

A third disadvantage of the prior art system of FIG. 3 lies in the necessity of detecting absolute values of light energy in the incident and reflected beams which vary only slightly for different thicknesses of film sample. This is illustrated in FIG. 4 which shows a representative relationship between the magnitude of detected energy versus film thickness. It can be seen from this figure that even slight errors in the determination of detected reflected energy can cause great differences in the determined film thickness.

These specific disadvantages of a typical prior art measuring device, in addition to those discussed in the preamble to this specification, are overcome in the present invention by the application of the concepts to be discussed hereinafter.

One of the characteristics of the present invention is that the sample is impinged by light beams from more than one angle of incidence. FIG. 5 is illustrative of some considerations to be taken into account when dealing with different angles of incidence. First, so that the incident beam can be positioned at precisely the desirable point on the sample 2, and to assure that the angle of incidence is proper and stable, a servo system may be provided.

Schematically shown in FIG. 5 is a means by which the position of the sample can be maintained in elevation and in both horizontal attitudes, i.e. pitch and roll.

The operation of the system of FIG. 5 depends upon partial reflection of the light beam striking partially reflecting mirror 8C (before the beam 5 strikes split detector 8A and B) and retroreflected back toward beam splitting cube 7, the retroreflected energy being detected by quadrant photodetectors 11A, 11B, 11C, and 11D.

The sample in FIG. 5 is shown in three different positions. The solid position is the normal position for measurement, the long and short dashed representation indicating a raised out-of-calibration position, and the dashed lined representing a tilted position. In the normal position of the sample 2, the incident beam 3 reflects from the surface at point 10B and is received on photodetector 8A and 8B as beam segment 5. For the sake of simplicity of the drawing, the beams in FIG. 5 are drawn as line thicknesses, while in fact they are of a diameter on the order of a millimeter so that beam 5 actually spans the slit between photodetectors 8A and 8B. Thus, when sample 2 is properly positioned, an equal amount of light is received on photodetectors 8A and 8B such that the outputs 93 will be sensed at the photodetector amplifier 75 and differential amplifier 77 as equal signals, resulting in no error signal being sent to servo processor 81.

Similarly, the retroreflected beam traverses a path coincident with incident beam 3 and produces beam segment 5f which spans the gap between photodetector 11A,C and 11B,D to produce equal outputs on lines 91 and in turn, to produce equal outputs of photodetector amplifier 71 and diff amp 73, resulting in no error signal being sent to servo processor 81.

Both pitch and roll servos will be described below by a representative term "tilt", since the implementation of both pitch and roll servos are virtually the same. It will be understood that the photodetector amp 71 can perform signal summing so that detectors 11C and D acting together and 11 A and B acting together can be effective to represent pitch detectors, while 11A and C acting together and 11 B and D acting together can be effective to represent roll detectors. Diff amp 73 is, then, a dual diff amp, one used for pitch and one for roll. The use of a quadrant photodetector in this manner is known from the videodisc player tracking art, and its implementation in the present invention is assumed to be well within the ability of the skilled worker without further technical description.

Assuming the system has been previously calibrated, with no error signals developed and sent to servo processor 81, the tilt servo 85 and elevation servo 87 (which, respectively, have mechanical movements coupled to the specimen 2 for tilting, and raising or lowering specimen 2) are locked in normal position.

However, if specimen 2 is raised, due to vibration, temperature changes of the sample mounting equipment, inadvertent bumping, etc., or if a new sample having a thicker substrate than the previous one tested is moved into position, the incident beam 3 will be reflected as beam segment 5b and on to photodetector 8A. Since more energy will now be on photodetector 8A than on 8B, an error signal will be developed, using standard circuit techniques, in diff amp 77 which will then send an error signal to servo processor 81 and a further drive signal to elevation servo 87 to lower the platform 89 and regain an equal output from photodetectors 8A and B. Note should be made of the fact that with the movement of the sample upwardly, the retroreflected beam from either normal or elevated position traverses the same path 3 back to cube 7 and photodetectors 11A and B with no difference in outputs thereof on lines 91 being developed.

Accordingly, with motion of the sample either up or down, the closed loop servo system comprised of photodetectors 8A and B, photodetector amp 75, diff amp 77, servo processor 81, and tilt servo 85 serves to maintain a fixed predetermined vertical position for the sample.

In a somewhat different manner, when the sample 2 is tilted, the incident beam 3 is reflected as beam segment 5a which is no longer perpendicular to the surface of photodetectors 8A and B. Consequently, the retroreflected beam 5c is at an angle of reflection equal to the angle of incidence of segment 5a so as to strike the sample 2 toward the left in FIG. 5, creating a beam segment 5d along a skewed path instead of the normal path along incident beam 3. The angles chosen for representation in FIG. 5 are greatly exaggerated to illustrate the concept. However, it can be appreciated that only minute angular changes will be permitted in order to be able to maintain accuracy of the measurement of film thickness. Accordingly, the beam segment 5e is representative of that portion of the angularly directed segment 5d which reflects from the beam splitting cube 7 and concentrates the beam 5e more onto photodetector 11A than on 11B resulting in a differential output from diff amp 73 and an ultimate servo drive signal to tilt servo 85.

As may be observed, while the change of elevation has no effect on the output of photodetectors 11A and B, the tilting of the sample has a positive effect on the output of photodetectors 8A and B. However, a timer 83 is provided to pace the frequency of error correction through each servo system, and more specifically, the timer 83 cycles the tilt servo much faster than the elevation servo by a factor of, for example 10 to 1, so that any change of outputs from photodetectors 8A and B will be much slower than those from 11A and B. With this arrangement, if a change in elevation of the sample occurs, since no error outputs from detectors 11A and B will exist, the elevation servo 87 will ultimately make the appropriate correction to satisfy the closed loop equation. On the other hand, if a tilting of the sample occurs, there will be a differential output from both diff amps 73 and 77. However, since the tilt servo 85 reacts substantially faster than the elevation servo, by the time the elevation servo would respond to a drive signal to effect correction, the tilt servo would have already reacted to the change in output of photodetectors 11A and B, and thus, the change in output of photodetectors 8A and B will be essentially non-effective. In this way, the tilt and elevation servos are substantially independent of one another, and since it is not expected that the elevation of the sample will change very abruptly, there is no disadvantage to establishing the different cycle times for the two servo systems. Obviously, rather than providing a timer for establishing different sampling rates for the two servo subsystems, the photodetector amplifier electronics 71 and 75 and/or the diff amps 73 and 77 could merely be designed to have different frequency responses to input changes from their respective photodetectors. The same ratio of 10 to 1 for tilt-to-elevation servo frequency response would be required to substantially electronically isolate the two servo subsystems from common mode fluctuations.

Figure 6:
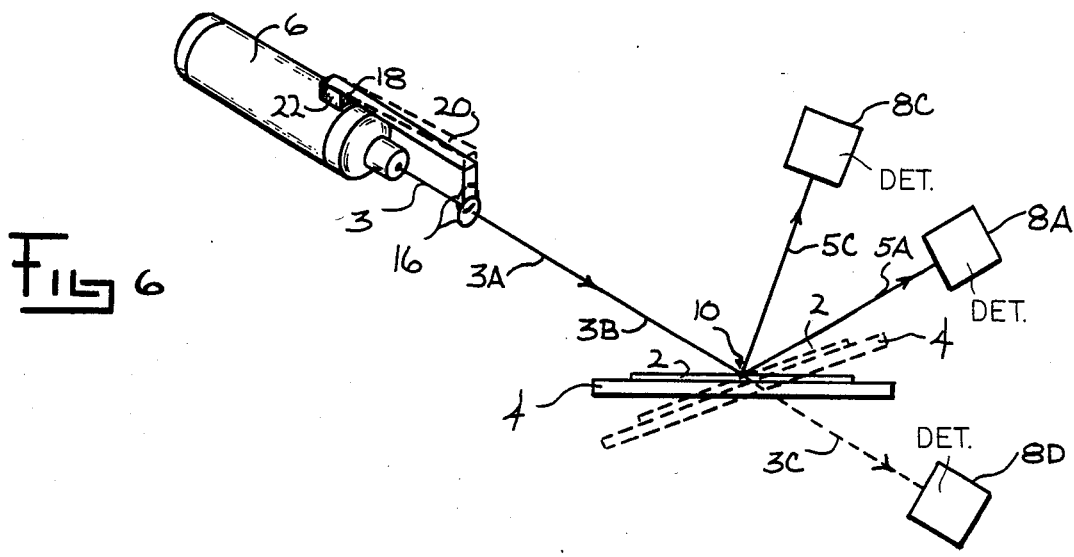
FIG. 6 is a system concept for varying the polarization angle of the incident energy beam in time and at two different angles of incidence to the sample surface.

Basically, the thickness measuring technique according to the present invention involves the use of or detection of a variably polarized energy beam impinging upon the surface of the sample to be measured and at more than one angle of incidence. From the combination of these two basic elements, the unique concepts and advantages of the present invention become evident. In FIG. 6, a basic form of the invention is shown. In this figure, a laser source 6 providing an incident beam 3 impinges sample 2 at a prescribed angle of incidence as shown by the angle between the incident beam 3 and the surface of the solid view of sample 2. The angle of reflection, equalling the angle of incidence, causes the reflected beam 5A to be intercepted by photodetector 8A. As the incident beam 3 leaves the laser 6, it passes through one or the other of polarizing plates 16 mounted on the end of arm 20 of a vibrating tine 18 actuated by a motor 22. The two polarizing plates 16 have their polarization angles at 90 degrees to one another so that the beam 3 emanating from the laser 6 is alternately polarized in quadrature relationship at 3A in FIG. 6. Beam 3A passes through beam splitter 24 and exits as beam 3B unaltered in its direction of incidence toward sample 2.

In order to calibrate the system of FIG. 6, the sample may be removed to allow beam 3B to pass directly onto photodetector 8D as shown in FIG. 6 along a path indicated by the designation 3C. Since photodetector 8D intercepts all of the incident beam energy, the ratio of S to P measured in this condition can be used to divide into the S to P ratio measured later with the sample inserted to arrive at the change in S to P ratio contributed by the sample.

Note should be made of the fact that photodetector 8D is also used as the sample detector (instead of 8A or 8C) in a transmissive measurement system.

After calibration, the sample may be inserted into position, and at the angle of incidence shown by the solid representation of sample 2, photodetector 8A will indicate a particular output for each of the times during which polarizing plates 16 are in the optical path of the incident beam.

In the ensuing description of the invention, the two polarization angles of the incident or reflected beam or beams will be assumed to be at 90 degrees to one another, although any other angle of separation is possible, the mathematics and calculating times and procedure merely being simplified by orienting the two angles of polarization in quadrature. Moreover, in the description which follows, one polarization angle will be assumed to be oriented parallel to the plane of the surface of sample 2 and designated as the S polarization angle, while the other angle of polarization, oriented perpendicular to the planar surface of sample 2 will be designated as the P polarization angle.

Continuing with the embodiment of FIG. 6, photodetector 8A has an output which alternately represents the magnitude of the reflected energy in beam 5A for the S and P polarization angles of the incident beam. By tilting the sample 2 to the dotted position shown in FIG. 6, the reflected beam 5C is produced and intercepted by photodetector 8C. Multiple detectors may be used, or a simple movable carriage may be provided to rotate a single photodetector into position 8A and 8C, if desired. The separate detectors are shown in FIG. 6 (and elsewhere) for simplifying the drawing and explanation. If convenient, multiple detectors may be used without sacrifice of accuracy. Since only ratios of S to P are needed, the absolute responsivity (light in to signal out) is unimportant.

Thus, the output of photodetector 8C also produces a representation of alternate S and P orientation responses, but with different values for each due to the different angle of incidence with respect to the sample surface. As explained in connection with FIGS. 1 and 2, not only are the energy levels between the intercepted S and P oriented beam components different from each other for the same angle of incidence, they are likewise different from each other for a different angle of incidence and, more importantly, have different ratios of magnitude for the two different angles of incidence. That is, the ratio of S to P in the reflected beam 5A is different than the ratio of S to P in the reflected beam 5C, and, of course, different than the ratio of S to P in the calibration beam 3C.

Recalling the effects of constructive and destructive interference of the beams 5A and 5C leaving the surface of sample 2, and recognizing the obvious fact that the thickness of the sample has not changed, an exact, but complex, mathematical relationship can be formulated for determining the film thickness of sample 2 from the two values of S/P (ratio of S to P) for the two angles of incidence. Expressing this concept in a non-mathematical relationship, it can be appreciated that, if all parameters of the system of FIG. 6 were known, i.e., film thickness, index of refraction, and angles of incidence for the incident beam having S and P components, a particular value for S/P for each of the two angles of incidence can be determined. Likewise, if one of the parameters is unknown and S/P is measured, the value of the unknown parameter can be inferred.

It is important to note that, due to losses in the system, (to be explained later), it is not possible, with any accuracy, to predict the absolute magnitudes of S and P of the reflected beam for each angle of incidence. By using the ratio of S to P, however, absolute values for the reflected beam components is not necessary; any defect on the sample at the point of impingement of the incident beam will contribute equally to both S and P and not affect the ratio of the two; and any system drift such as that of the detector is eliminated provided that the rate of change of polarization plates 16 is reasonably high relative to the rate of system drift. In this respect, system drift insofar as temperature, power supply variances, and the like are concerned, is relatively stable over any 1 second interval, and thus a vibration rate of arm 20 in FIG. 6 on the order of 1 Hz to 100 Hz reduces the contribution of system drift in the final calculations to an insignificant number.

Photodetector 8D can be employed to intercept the non-sample path of the incident beam and provide an accurate calibration of the ratio of S to P of the incident beam prior to reflection by the sample. Such information would enter into the calculation of the film thickness as determined by the S/P ratios derived from the output of photodetectors 8A and 8C as heretofore suggested.

Mathematically speaking, by using time-shared S and P polarization orientations and two angles of incidence, two equations in two unknowns can obviously be set up. Thus, in the example of FIG. 6, not only can the thickness of the film be determined, but an unknown index of refraction of the sample can also be determined. It must be borne in mind, however, that when the optical thickness of sample 2 exceeds one-half wavelength of the incident light beam, the formula for calculating film thickness may have two discrete solutions, and it can be easily demonstrated by basic optical analysis that a continuously variable film thickness would create a cyclical waveform for S/P ratio values. For example, the S/P ratio has the same or nearly the same value for an optical thickness of one-quarter wavelength as for an optical thickness of three-quarters wavelength, five-quarters wavelength, etc. To be precise, then, the set of equations defining the relationships in FIG. 6 actually define three unknowns. The third unknown (precisely where on the cyclical curve the actual thickness is represented) can readily be ascertained by merely providing a third angle of incidence and a third photodetector having S/P ratio outputs. It is within the knowledge of the skilled worker, however, that typical applications for film thickness measuring devices often involve only fractional wavelength variations to be determined from sample to sample.

Thus, while a uniquely defined determination of film thickness and index of refraction for the diagram of FIG. 6 would involve three angles of incidence, in a typical application where the range of thickness is known to within fractional wavelength values, only two angles of incidence are required.

Figure 7:
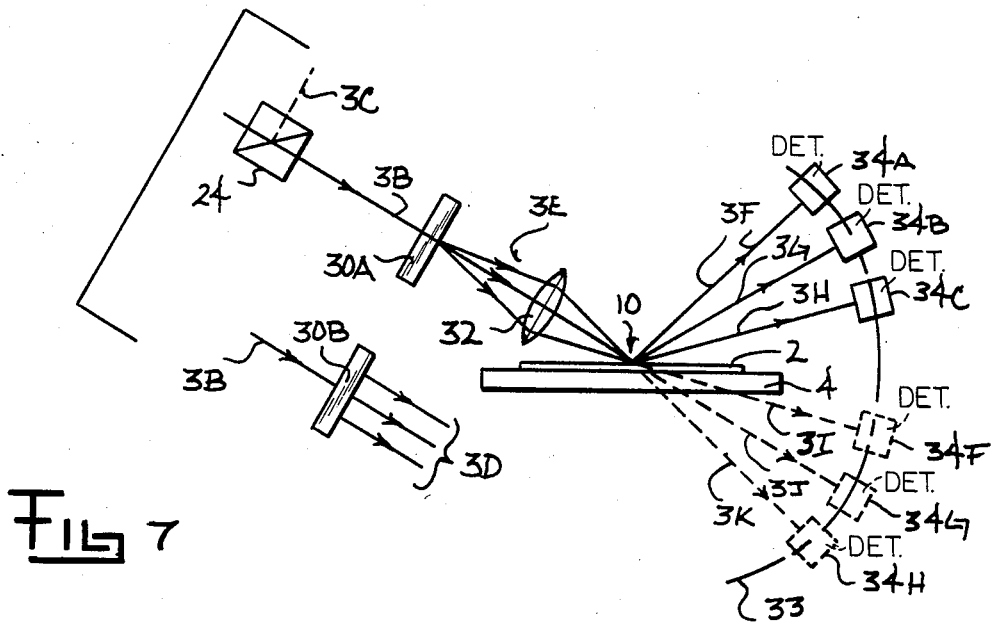
FIG. 7 shows a preferred arrangement for providing a plurality of incident beams each at a different angle of incident to the sample surface, as well as an arrangement for calibrating the system with the sample removed.

FIG. 7 illustrates the manner in which an incident beam 3B may be split into multiple components 3E, by a device 30A which may be any type of beam splitter such as a diffraction grating. The diverging beams 3E, passing through the condensing lens 32, are caused to converge and meet at a point 10 on the surface of sample 2. Individual reflected beams 3F-3H are intercepted by photodetectors 34A-34C, preferably aligned along a circular path 33 so as to provide the three outputs when three unknowns are to be determined, or when redundancy calculations are desired. Beams 3I-3K and detectors 34F-34H have the same function as beam 3D and detector 8D of FIG. 6. Again here, each detector 34A-34F may, in a practical arrangement be a single repositionable photodetector. An alternative device for splitting the beam 3B into multiple beam segments is shown in FIG. 7 by the beam splitter 30B.

Figure 8:
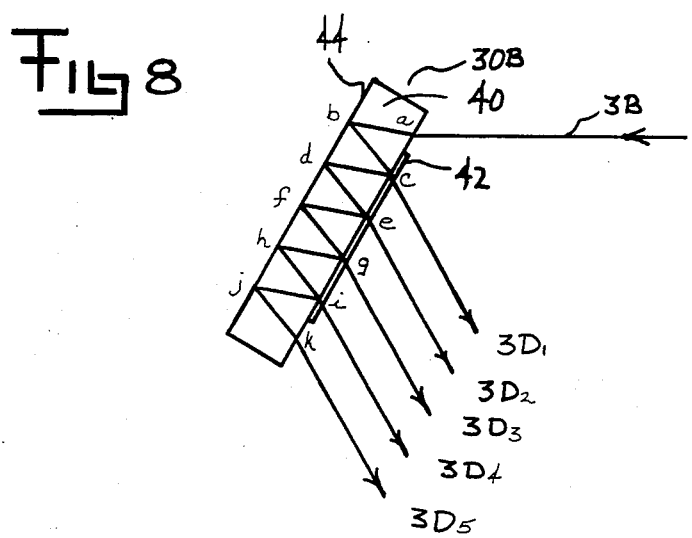
FIG. 8 illustrates a novel beam splitting device for producing a plurality of parallel beams of equal energy from a single source beam.

Beam splitter 30B of FIG. 7 is merely a schematic representation of the device of FIG. 8 which has a single incident beam 3B and a plurality of parallel output beams 3D1-3D5. The beam splitter 30B comprises an optically transparent block 40 having a highly reflective back surface 44 and a partially reflective front surface 42. The incident beam 3B enters an area of block 40 not covered by layer 42, and a standard refraction of the incident beam occurs at point a as shown in FIG. 8. Substantially one hundred percent reflection of the incident beam occurs at b and partial reflection at c. A similar effect can be appreciated for the other points of impingement of back surface 44 and front surface 42. Since the front surface 42 is only partially reflective, a certain percentage of the beam segment bc exits the block 40 as beam segment 3D1. Except for the minor losses of light energy as the beam travels through the transparent block 40, each of the five output beam segments 3D1-3D5 are of substantially equal light energy value and, of course, parallel to one another. In a sophisticated preferred embodiment of the invention, five such beam outputs are indeed utilized by the system, four of the beam segments being used for determining the S/P ratios, and one of the beam segments being used as the reference beam in the tilt and elevation servos of FIG. 5.

In order to provide equal light intensity for the five output beam segments, the partially reflective coating 42 exhibits variable reflectivity from points c to i, the reflectivity progressively decreasing in the direction toward point i. For example, equal outputs can be realized by making the reflectivity at points c to i as follows (ignoring minor internal losses):

|          | reflected | transmitted | reflectivity |
|----------|-----------|-------------|--------------|
| at point c | 80%     | 20%         | 80%          |
| e        | 60%       | 20%         | 75%          |
| g        | 40%       | 20%         | 67%          |
| i        | 20%       | 20%         | 50%          |
| k        | 0%        | 20%         | 0%           |

Alternatively, since only S/P ratios are needed for each incident beam angle, there is no absolute necessity for each beam segment $3D_1$–$3D_5$ to be equal. Thus, if a constant reflectivity were used for partially reflective surface 42 to permit a reasonable light intensity for the least intense beam segment exiting splitter 30B, say about 10%, then using a constant reflectivity, of for example 60%, for surface 42 will produce the following approximate light intensity levels for the five beam segments $3D_1$–$3D_5$:

|          | reflected | transmitted | reflectivity |
|----------|-----------|-------------|--------------|
| at point c | 60%     | 40%         | 60%          |
| e        | 36%       | 24%         | 60%          |
| g        | 22%       | 14%         | 60%          |
| i        | 13%       | 9%          | 60%          |
| k        | 0%        | 13%         | 0%           |

Realizing that more light is reflected from the sample at greater angles of incidence, i.e. the greater the angle from normal the more light that is reflected, it is advantageous to purposely have uneven light levels for the separate beam segments, the stronger one being used for the beam segment at the smallest angle of incidence.

Figure 9:
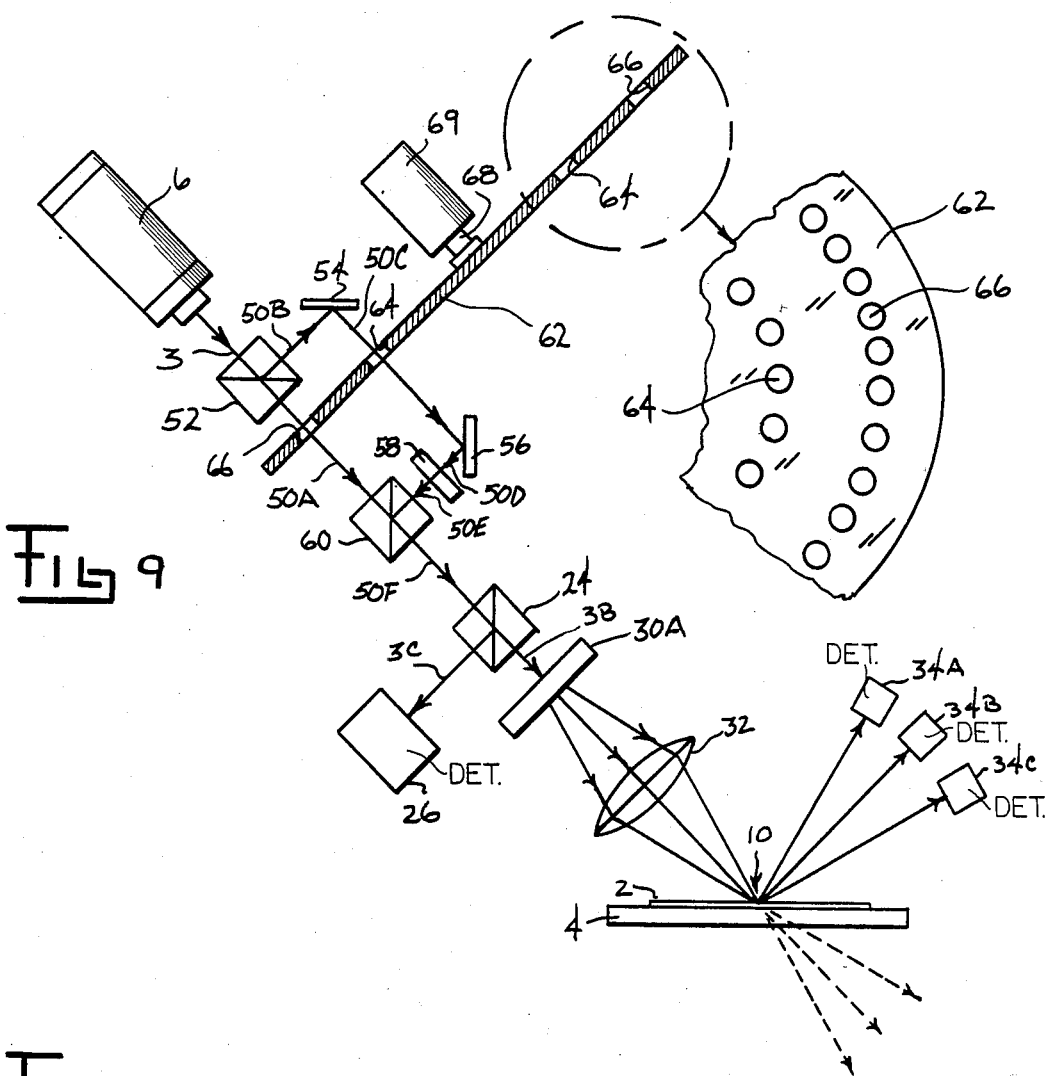
FIG. 9 shows an alternate scheme to that of FIG. 6 for producing time shared alternating beams of different polarization angles, in accordance with the present invention.

An alternative embodiment of the invention can be seen by reference to FIG. 9. The arrangement in this figure uses a rotating disc 62, supported by a shaft 68 and rotated by a motor 69, to implement the time-shared alternate S and P polarization angles. Specifically, a first series of apertures 66 are evenly spaced at a first radius of the disc 62, each aperture 66 receiving a beam 50A having a first polarization angle. Each of a second series of apertures 64 at a different radius receive a beam 50C which passes through polarization plate 58 to orient the polarization angle of beam 50E at 90 degrees to the polarization angle of beam 50A. Providing a different number of apertures 66 relative to the number of apertures 64 permits the determination, at the photodetector intercepting the reflected beam from the sample, of which beam polarization is being sensed by using FM discrimination techniques. That is, since the reflected beam is pulsating at one of the polarization angles at a different frequency than the other, it is well within the knowledge of the skilled worker to FM discriminate the conposite detected signal and determine which of the two angles is being received at any point in time due to the different frequencies of occurrence. In FIG. 9, the number of apertures 64 is exactly half the number of apertures 66 to exemplify this aspect of the present invention. Other techniques, such as providing a tachometer signal derived from the disc itself can also be used to determine which polarization angle is being received at any point in time, thereby negating the necessity of having a different plurality of apertures 64 than apertures 66. Since tachometer meter synchronization techniques are well known in the art, no discussion of any particular type of tachometer system will be discussed herein.

In any event, as noted in FIG. 9 by the optical subsystem comprised of beam splitting cubes 52 and 60 and mirrors 54 and 56, the incident beam 3 is split into two parallel beam segments 50A and 50C. The laterally directed beam segment 50B from beam splitting cube 52 strikes mirror 54 and passes through the inner radius of the disc 62 through aperture 64, and is polarized by polarizing plate 58. The non-deflected segment 50A of the incident light beam passes through the outer radius of disc 62, and the two beams combine at beam conditioning cube 60 to form the composite beam 50F. In order to produce polarization rotation, the polarization rotator 58 is positioned in the optical path of beam segment 50D, so that the altered beam segment 50E is combined with segment 50A in the appropriate relationship to produce the composite beam.

With the disc rotating at a rate in the range of 1 RPS to 100 RPS, the composite beam 50F comprises a time-shared series of alternating beam segments with alternate segments being polarized at right angles to one another, and by initial calibration of the optical arrangement, e.g., rotating laser 6 and polarization rotator 58, the aforementioned defined S and P polarized beam segments are produced. The beam splitting cube 24 and all downstream optical elements of FIG. 9 correspond in kind and function to those already discussed in connection with FIGS. 6 and 7.

Figure 10:
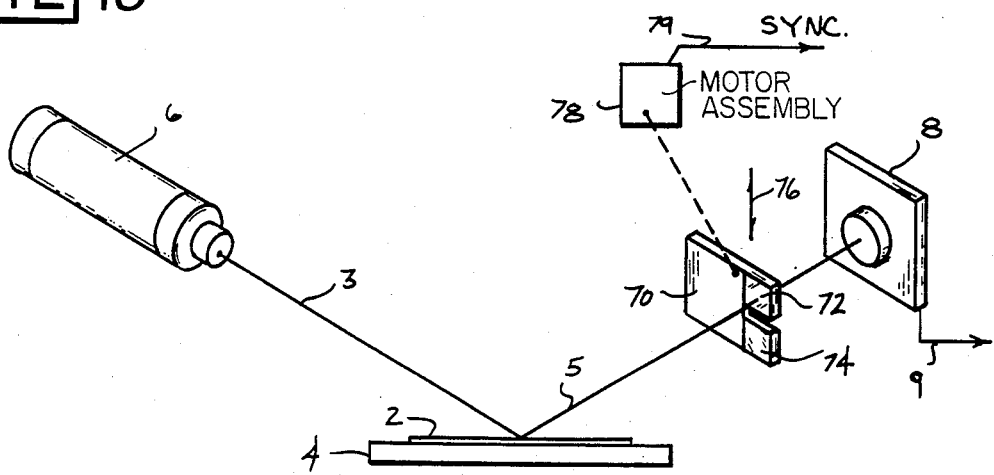
FIG. 10 shows a scheme for alternately sensing the reflected energy beam in a time shared relationship before reaching a common detector.

As mentioned earlier, one of the characterizing features of the present invention concerns the requirement for analyzing the effects on S and P polarized beam components as an incident beam strikes the surface of the sample under test. Whether the incident beam is split into S and P components or is directed at the sample and split into separate S and P components after reflection is incidental to the concepts insofar as analyzing the reflected beam or beams is concerned. FIG. 10, for example, shows a film thickness measurement system using an incident beam 3 of unpolarized light, circularly polarized light, or light linearly polarized at an angle, preferably 45°, to the polarization angle of polarization plates 72 and 74. The reflected beam 5 is intercepted before it reaches the detector 8, alternately by polarization plates 72 and 74 mounted on a reciprocating block 70 which moves in the direction of arrow 76 by a motor assembly 78. The motor assembly 78 outputs a synchronizing signal on line 79 to be used in the photodetection circuitry, along with the output 9 from photodetector 8 so that synchronization can be established. That is, it is necessary in the analyzing of the signal intercepted by photodetector 8 to know which polarity of polarization each segment of the beam intercepted by photodetector 8 exists at any point in time, and the sync signal on line 79 provides this information.

A preferred form of the invention will now be discussed in connection with FIG. 11 in which the incident beam 3 is continuously rotated in polarization angle by a hollow shaft motor 84. First, the polarized incident beam 3 passes through a circular polarization plate 80 to produce a circularly polarized beam 82. Beam 82 passes through the hollow shaft 88 of motor 84 powered by a power line 86. Housed in the hollow shaft 88 of motor 84 is a polarization plate 90 which rotates with shaft 88, at a rate in the range of about 10 RPS to 1000 RPS. As a result, the beam segment 92 has a continuously variable polarization angle angularly changing at the rate of rotation of shaft 88 of motor 84. Since the P and S polarization angles occur twice per revolution, the rate of sampling the S to P ratio will be at the rate of 20 to 200 per second.

Beam segment 92 is directed to the beam splitter 40 which was discussed in connection with FIG. 8. The five parallel beam segments $3D_1$-$3D_5$ pass through a condensing lens 32 and impinge upon the surface of sample 2 in the manner previously described.

In the embodiments of FIGS. 6 and 9, the energy beam incident upon the surface of sample 2 was structured to have alternating time-shared segments of beams strike the surface, each alternate segment in time being rotated 90 degrees with respect to its adjacent timewise spaced segments. Such optical assemblies provided one of the characteristics of the beam needed for carrying out the present invention, i.e., that of providing alternating S and P components of the incident (or reflected) beam.

Figure 11:
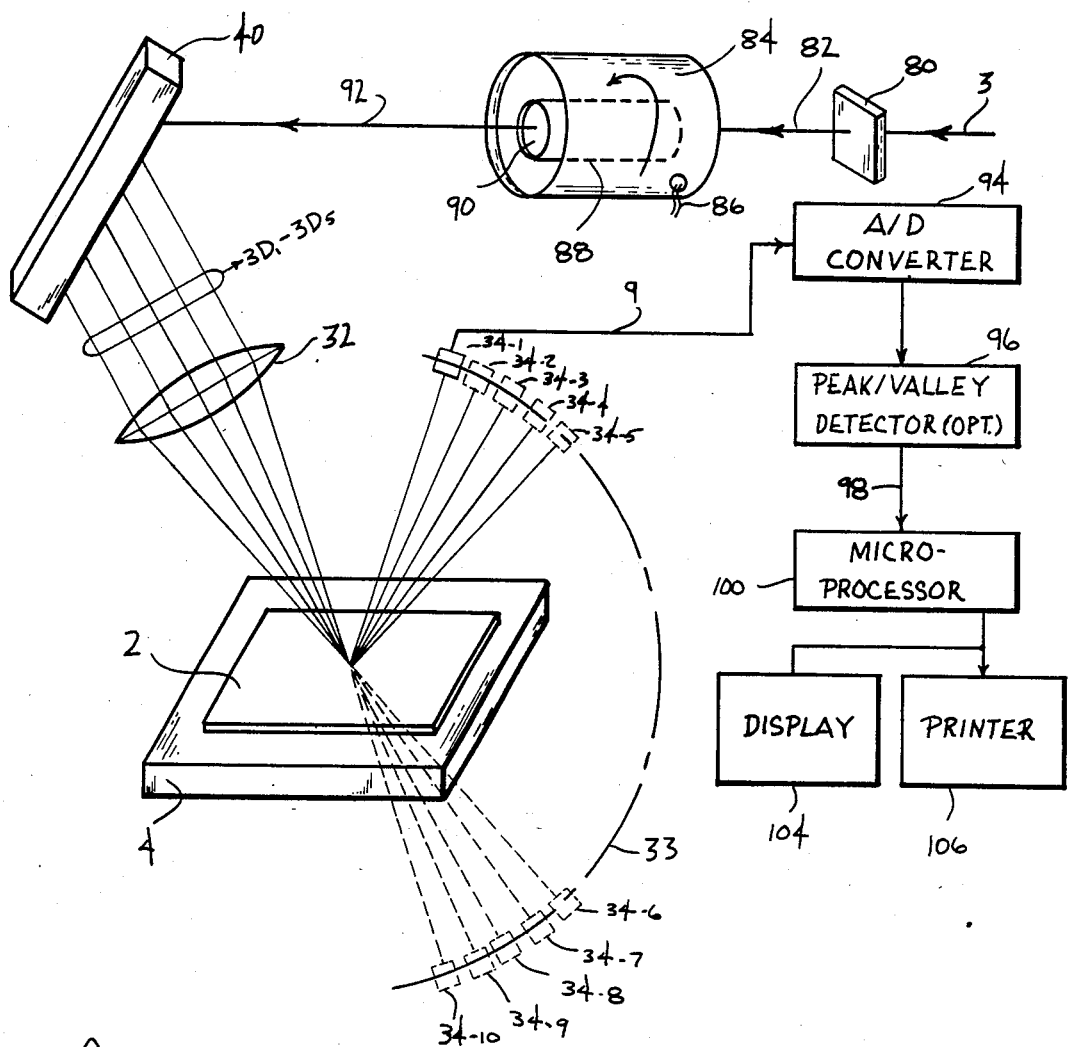
FIG. 11 shows an alternate scheme to those of FIGS. 6 and 9 for producing an incident source beam having a continuously varying polarization angle, in combination with the beam splitter shown in FIG. 8.

In the embodiment of FIG. 11, rather than producing alternate beam segments of discrete angular differences, the beam segment 92 is continuously variable between the S and P polarization angles. It may be noted in FIG. 11 that no calibration devices are needed, since discrete polarization angles of the incident beam are not required. That is, since the angle of polarization of beam segment 92 is continuously varying, regardless of the angular orientation of the initial laser device or other optics in the path of the beam striking the sample 2, at some point in time, being continuously variable, the beam polarization angle will be at the S polarization angle, i.e., parallel to the plane of the surface of sample 2, and at another time will be at the P polarization angle, i.e. when the electric field of the incident beam is normal to the surface of sample 2. After reflection from sample 2, either separate photodetectors 34 or a single photodetector moved along a line 33 to positions 34-1 through 34-10 are employed.

Recalling that the thickness of the sample 2 is finally determined by measuring the S/P ratios at the different angles of incidence, the arrangement of FIG. 11 is unique to the extent that discrete S and P polarization angles do not exist in the incident beam. However, as the beam is rotated in polarization angle by motor 84, there is obviously some point in time when maximum reflection occurs from the sample 2, that is, when the S polarization angle occurs. Similarly, as the polarization angle of the beam is rotated by motor 84, there is some point in time when the light reflected from the sample of sample 2 is a minimum, and this, of course, occurs when the polarization angle of the incident beam is precisely the P polarization angle (note should be made of the fact that for certain materials maximum reflection occurs at the P angle and minimum reflection occurs at the S angle).

Again having reference to FIG. 1, if one were to consider only the S component of the reflected beam, and assuming an angle of incidence of approximately 45 degrees, it can be seen from FIG. 1 that the S component (S1) is approximately 10 percent while on the other hand, measurement of only the P component would indicate a surface reflection of approximately 1 percent. This results in a S/P ratio of 10.

Over a period of time, then, it can be appreciated that the magnitude of detected reflected energy in the S polarization orientation will vary from a maximum of 10 percent reflected energy (when the polarization angle is in the S direction) to a minimum of 1 percent (when the polarization angle is in the P orientation). This is shown in FIG. 12 by the dashed line 112 showing the S polarization response as it would be if measured with a detector detecting only the energy reflected from the surface of sample 2 parallel to the plane of the surface of sample 2 (assuming a fixed angle of incidence).

Figure 12:
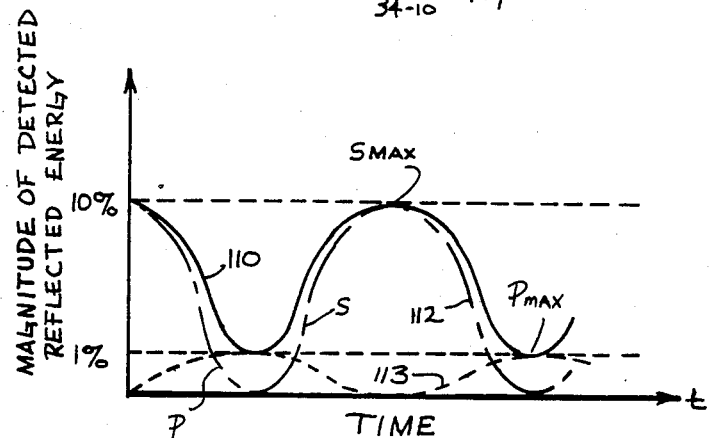
FIG. 12 is a graphical representation of the relationship between S and P polarized light beam components as a function of time in the measurement cycle.

Similarly, using a photodetector and polarization plate which would measure only the energy in the P polarization orientation, i.e., normal to the surface of sample 2, a waveform similar to that of 113 of FIG. 12 would show the dashed curve representing the energy reflected in the P orientation. On the other hand, if a photodetector were used to merely intercept the reflected beam without any polarization bias, the sum of the two waveforms 112 and 113 of FIG. 12 would be produced. This is shown as the solid line 110 in the figure representing the algebraic sum of the two curves 112 and 113. By passing the output of the photodetector to a circuit which can detect peaks and valleys of an input analog signal, the peak of the waveform 110 would represent the S component of reflected energy, while the valley of waveform 110 would represent the P component of energy. A ratio of S to P could then be performed in carrying out the operation of the present invention. In FIG. 11, an analog-to-digital converter 94 is used to digitize the analog waveform 110 and convert it to a series of digital representations which can be operated on by any number of a variety of available digital microprocessors to find the peak and valley points of waveform 110. In FIG. 11, a representation circuit defined as a peak/valley detector 96 is shown, the output 98 being converted to discrete S and P representations, for example with known sample-and-hold circuitry, for use in the ultimate microprocessor calculation function. Again, representative, a microprocessor 100 operates on the S and P levels for each angle of incidence and outputs the result to a printer 102 or display 104 in a manner well known to those skilled in the art of microprocessor technology.

In summary, it is an object of the present invention to provide a method and means for measuring the thickness and optical characteristics of a sample of material using optical techniques heretofore unknown. Optical assemblies have been illustrated and described in which the ratio of S to P for a number of angles of incidence, and the significance of the ratios of S to P for each incident angle have been explained.

The advantages offered by performing the method according to the invention is not merely an extension of that which is known in the prior art, since substantial advantages not possible with prior art techniques are evident. Among the major advantages are: the lack of need for measuring absolute magnitudes of reflected energy; the avoidance of inaccuracies encountered in the use of multiple light sources or multiple detectors; the avoidence of drift parameters by changing between the S and P polarization angles at a rate substantially higher than the rate of change of system parameters due to drift; the ability to either increase the accuracy of any thickness determination, provide a redundant calculation information, and/or permit determination of the index of refraction of an unknown film of an unknown thickness; are all possible without any concommitant disadvantages.

The actual calculations necessary to produce the final thickness and/or index of refraction results can be performed by the artisan using available technology. It is presumed that, especially with the variable polarization angle configuration of FIG. 11, a microprocessor aided analysis would be of substantial benefit.

Using the definition of "distortion" as a change in some characteristic of the light beams used in the analysis of film thickness, a broad general statement regarding the present invention can be proposed. If energies in two distinguishable modes (e.g., S and P polarization angles), whose parameter ratios (or equivalent) are known, are transmitted by a process which causes an equal percentage of amplitude distortion (surface defects, drift, etc.) of the two energies, and if simultaneously a second parameter distortion of predictable characteristics (e.g., thickness or index of refraction effects) for each energy mode transmission is present, then a formula relating all possible absolute transmission distortions (gains or losses) of one mode for any absolute transmission parameter distortion of the other mode can be determined by a measure of the power ratio of the two transmitted energies, so long as the transmission process is sensibly less than totally absorbing. Additionally, if the transmission system amplitude distortion varies as a known function of some system parameters (such as thickness, index of refraction, etc.), then by taking N measurements of transmitted power ratios while varying one or more system parameters (e.g., angle of incidence) in a known fashion, N other system parameters with single valued transmission distortion functions can be calculated.

In the case where the desired parameter has a cyclical transmission distortion function, the number of power ratio measurements required depends on the range of desired parameter, and the nature of the transmission distortion function of the varied parameter(s). The accuracy obtainable depends, in general, on the sensitivity of transmission of the system to the particular parameter(s) involved and the accuracy of the power ratio measurement(s).

In this connection, it is much simpler to determine the ratio of two transmitted powers (especially if they occur simultaneously or interleaved in time at a rate much greater than transmission system amplitude drift) than to determine the absolute transmission distortion with an accuracy yielding comparable parameter accuracy.

The invention described above provides quick and accurate measurements of thickness and index without concern for the dispersion characteristics of the sample. This is made possible by using S to P ratios and a source beam of one wavelength. Variation of incident angle for the single wavelength beam gave rise to the determination of additional characteristics of the sample and/or added more sensitivity to the measurement. In this connection, some thin film materials, such as $SiO_2$ on Si, demonstrate a rather constant index of refraction for a variation of wavelength of incident light, i.e. the dispersion factor is insignificant. For such materials, multiple fixed wavelength energy beams could be substituted, in the invention, for the multiple angles of incidence, to provide an alternate mathematical model to determine the same parameters. That is, when dispersion is not a factor, instead of using N angles of incidence of the beam, N different wavelengths of incident light can be used with the same analytical results. For convenience, instead of merging multiple beams from different wavelength energy sources, advantage could be taken of known devices which inherently radiate multiple fixed wavelength energy beams, such as certain Helium-Neon lasers which can be made to radiate laser light at 0.633 microns, 1.152 microns, and 3.391 microns by selective mirror coating techniques. With multiple fixed wavelength beams, only the mathematical model need be changed to relate S to P ratios to thickness and/or index as hereindescribed. The arrangement of FIG. 6 may be provided with source 6 of multiple fixed wavelength laser beams and with the specimen maintained at a fixed angle with respect thereto.

In the embodiments of FIGS. 6–10, the beam issuing from the beam source may be unpolarized, circularly polarized or polarized at an angle, as would best suit each embodiment. In FIGS. 6 and 10, for example, a linearly polarized light source, preferably at 45° to the angles of polarization of the two alternate plates in each embodiment, would provide appropriate S to P ratios.

The arm 20 holding the two polarization plates 16 of FIG. 6 could be replaced with a similar arm 20 having a single polarization plate 16 which passes alternately into and out of the path of beam 3 to produce a polarization angle varying beam 3A of a character similar to that of beam 50F of FIG. 9, also employing a single polarization plate.

In the description of FIG. 2, supra, only first order reflections within the body of the samples measured were considered. Obviously, in addition to the beam rays shown and described in connection with FIG. 2, there are second order ray elements reflecting from the underside of the top surface 2' as the beam portion AB (and similar ray elements) passes upwardly in FIG. 2. As can be appreciated, even this reflection will be again reflected off of surface 4', producing third and higher order contributions to the final intensity and phase characteristics of the composite beam leaving sample 2. Dependent upon the desired degree of accuracy, these higher orders of reflections may be taken into account in the calculations for thickness and index of refraction using an infinite series solution, as is done in the example which follows.

From the foregoing, it can be readily realized that this invention can assume various embodiments. Thus, it is to be understood that the invention is not limited to the specific embodiments described herein, but is to be limited only by the appended claims.

I claim:

1. A method for measuring the thickness of a thin material sample having a transmission efficiency of greater than zero for an impinging beam of radiant energy, said sample having a given, but not necessarily known, index of refraction at said given wavelength; said method comprising the steps of:
   providing a source beam of radiant energy of a single given wavelength;
   linearly polarizing said source beam in a predetermined direction;
   varying the polarization direction of the beam to produce, in time shared relationship, a first linearly polarized component of the beam orientated in a first direction, and a second linearly polarized component of the beam orientated in a second direction angularly displaced from the first direction;
   directing the polarization-varying beam onto an entry surface of the thin material sample at a first predetermined angle with respect thereto;
   detecting and analyzing the beam reflected by the sample at said first predetermined angle to determine the relative amplitudes of reflected first and second polarized components;
   directing the polarization-varying beam on the entry surface of the thin material sample at a second predetermined angle with respect thereto;
   detecting and analyzing the beam reflected by the sample at said second predetermined angle to determine the respective amplitudes of reflected first and second polarized components;
   comparing the ratio of first-to-second component amplitudes at said first predetermined angle with the ratio of first-to-second component amplitudes at said second predetermined angle; and
   determining the thickness of sample from a mathematical model equating thickness to a relationship between said wavelength of the source beam, the angular values of said first and second predetermined angles and said first and second component amplitude ratio comparison.

2. The method as claimed in claim 1, wherein said first and second polarized components are at right angles to each other and define S and P beam components, respectively.

3. The method as claimed in claim 1, wherein:
   said step of varying includes alternately passing the source beam through two different optical paths and altering the polarization angle of the beam as it passes along at least one of the paths to produce said first and second beam components, and merging the two beam components into a single beam path, prior to said directing steps.

4. The method as claimed in claim 1, wherein said varying step includes alternately inserting into the path of said source beam, first and second polarization plates having their directions of polarization at right angles with respect to each other.

5. The method as claimed in claim 1, including, prior to said directing steps, the steps of:
   splitting the source beam into two separate source sub-beams and issuing said sub-beams along separate paths; and
   converging said sub-beams so as to meet at the point of impingement upon said sample, thereby automatically carrying out said first and second-mentioned directing steps.

6. The method as claimed in claim 1, wherein said varying step includes passing the linearly polarized light from said light source alternately through two polarizing plates oriented at right angles with respect to each other to produce said first and second linearly polarized components.

7. A method for measuring the thickness of a thin material sample having a transmission efficiency of greater than zero for an impinging beam of radiant energy, the method comprising the steps of:
   directing a pair of single wavelength radiant energy beams onto an entry surface of the material sample, said sample having a given index of refraction at said wavelength, each beam having two components of different angles of polarization with respect to each other, and the two beams having different angles of incidence to said entry surface;
   detecting and analyzing the two beams reflected by the sample to determine the ratio of reflected energy for the two components of each beam; and
   determining the thickness of said sample from a mathematical model equating material thickness to a relationship between said given wavelength of the source beam, said given index of refraction, the angular values of said different angles of incidence, and the ratio comparisons of the amplitudes of said two beam components.

8. The method as claimed in claim 7, wherein said two polarized components are at right angles to each other and define S and P beam components respectively.

9. The method as claimed in claim 7, including the steps of:
providing a main source beam of radiant energy;
alternately passing the single main source beam through two different optical paths and altering the polarization angle of the beam as it passes along at least one of the paths to produce said pair of angularly displaced beam components; and
merging the two beam components into a single beam path, prior to said directing step.

10. The method as claimed in claim 7, including, prior to said directing step, providing a main source beam of radiant energy; and alternately inserting into the path of said main source beam, first and second polarization plates having their directions of polarization at right angles with respect to each other.

11. The method as claimed in claim 7, including, prior to said directing steps, the steps of:
providing a main source beam of radiant energy;
splitting the source beam into two separate source sub-beams and issuing said sub-beams along separate paths; and
converging said sub-beams so as to meet at the point of impingement upon said sample, thereby automatically carrying out said directing step.

12. Apparatus for measuring the thickness of a thin material sample having a transmission efficiency of greater than zero for an impinging beam of radiant energy, said sample having a given index of refraction at said given wavelength; said apparatus comprising:
a radiant energy beam source providing a beam of radiant energy of a single given wavelength;
means for polarizing said beam in a predetermined direction;
means for varying the polarization direction of the beam to produce, in time shared relationship, a first polarized component of the beam polarized in a first direction, and a second polarized component of the beam polarized in a second direction angularly displaced from the first direction;
means for directing the polarization-varying beam onto an entry surface of the thin material sample at a first predetermined angle with respect thereto;
means for detecting and analyzing the beam reflected by the sample at said first predetermined angle to determine the relative amplitudes of reflected first and second polarized components;
means for directing the polarization-varying beam onto the entry surface of the thin material sample at a second predetermined angle with respect thereto;
means for detecting and analyzing the beam reflected by the sample at said second predetermined angle to determine the respective amplitudes of reflected first and second polarized components;
a comparator for comparing the ratio of first-to-second component amplitudes at said first predetermined angle with the ratio of first-to-second component amplitudes at said second predetermined angle; and
processor means for determining the thickness of said sample from a mathematical model equating material thickness to a relationship between said given wavelength of the source beam, the angular values of said first and second predetermined angles and said first and second component amplitude ratio comparisons.

13. The apparatus as claimed in claim 12, wherein said first and second polarized components are at right angles to each other and define S and P beam components respectively.

14. The apparatus as claimed in claim 12, wherein:
said means for varying includes:
means for alternately passing the source beam through two different optical paths;
means for altering the polarization angle of the beam as it passes along at least one of the paths of produce said first and second beam components; and
means for merging the two beam components into a single beam path, prior to reaching said material sample.

15. The apparatus as claimed in claim 12, including first and second polarization plates, and wherein said means for varying includes means for alternately inserting into the path of said source beam, said first and second polarization plates with their directions of polarization at right angles with respect to each other.

16. The apparatus as claimed in claim 16, including:
means for splitting the source beam into two separate source sub-beams and issuing said sub-beams along parallel paths; and
means for converging said sub-beams so as to meet at the point of impingement upon said sample.

17. The apparatus as claimed in claim 15, including a pair of polarizing plates having their angles of polarization orientated angularly with respect to each other, and wherein said radiant energy beam source includes means for passing the beam of radiant energy alternately through said two polarizing plates oriented at right angles with respect to each other to produce said first and second polarized components.

18. Apparatus for measuring the thickness of a thin material sample having a transmission efficiency of greater than zero for an impinging beam of radiant energy, comprising:
means for generating a pair of single wavelength radiant energy beams;
means for directing the pair of radiant energy beams onto an entry surface of the material sample, said sample having a given index of refraction at said wavelength, each beam having two components of different angles of polarization with respect to each other, said directing means directing the two beams at different respective angles of incidence to said entry surface;
means for detecting and analyzing the two beams reflected by the sample to determine the ratio of reflected energy for the two components of each beam; and
means for determining the thickness of said sample from a mathematical model equating material thickness to a relationship between said wavelength of the source beams, said given index of refraction, the angular values of said different angles of incidence, and the ratio comparisons of the amplitudes of said two beam components.

19. A method for measuring the thickness of a thin material sample having a transmission efficiency of greater than zero for an impinging beam of radiant energy, said method comprising the steps of:

providing a source beam of radiant energy of a single given wavelength, said sample having a given index of refraction at said given wavelength;

polarizing the energy beam to have a first polarized component of the beam oriented in a first direction, and a second polarized angle oriented in a second direction angularly displaced from the first direction;

dividing the polarized energy beam to produce at least two separate rays of energy beam, each having said first and second polarized components and each having a beam axis angularly displaced with respect to its adjacent one;

directing the separate rays onto the entry surface of the thin material sample;

detecting and analyzing the separate rays reflected by the sample to determine the magnitudes of the reflected components of each ray;

comparing the ratio of first-to-second component amplitudes for each reflected ray; and determining the thickness of said sample from a mathematical model equating material thickness to a relationship between said given wavelength of the source beam, the angular values of each incident ray, and said first and second component amplitude ratio comparisons.

20. A method for measuring the thickness of a thin material sample having a transmission efficiency of greater than zero for an impinging beam of radiant energy, said method comprising the steps of:

providing a source beam of radiant energy of multiple fixed wavelengths and polarized in a predetermined direction, said sample having a given, but not necessarily known, index of refraction at said given wavelength;

varying the polarization direction of the beam to produce, in time shared relationship, a first polarized component of the beam orientated in a first direction, and a second polarized component of the beam orientated in a second direction angularly displaced from the first direction;

directing the polarization-varying beam onto an entry surface of the thin material sample at a predetermined angle with respect thereto;

detecting and analyzing the beam reflected by the sample at said predetermined angle to determine the relative amplitudes of reflected first and second polarized components of one wavelength;

detecting and analyzing the beam reflected by the sample at said predetermined angle to determine the respective amplitudes of reflected first and second polarized components of a second wavelength;

comparing the ratio of first-to-second component amplitudes at said first wavelength with the ratio of first-to-second component amplitudes at said second wavelength; and determining the thickness of said sample from a mathematical model equating material thickness to a relationship between said wavelengths of the source beam, the angular values of said predetermined angle and said first and second component amplitude ratio comparisons.

* * * * *